US006172237B1

(12) United States Patent
Labaw et al.

(10) Patent No.: US 6,172,237 B1
(45) Date of Patent: Jan. 9, 2001

(54) PROCESS FOR PREPARING EPROSARTAN

(75) Inventors: Clifford S. Labaw, Philadelphia; Joseph Robert Flisak, Lansdale; Li Liu, Collegeville, all of PA (US)

(73) Assignee: SmithKline Beecham Corporation, Philadelphia, PA (US)

( * ) Notice: Under 35 U.S.C. 154(b), the term of this patent shall be extended for 0 days.

(21) Appl. No.: 09/355,185

(22) PCT Filed: Feb. 13, 1998

(86) PCT No.: PCT/US98/02412

§ 371 Date: Jul. 27, 1999

§ 102(e) Date: Jul. 27, 1999

(87) PCT Pub. No.: WO98/35963

PCT Pub. Date: Aug. 20, 1998

Related U.S. Application Data

(60) Provisional application No. 60/038,195, filed on Feb. 14, 1997.

(51) Int. Cl.$^7$ .................................................. C07D 409/06
(52) U.S. Cl. .......................................................... 548/315.1
(58) Field of Search ........................................... 548/315.1

(56) References Cited

U.S. PATENT DOCUMENTS

| 5,185,351 | 2/1993 | Finkelstein et al. | .................. 514/341 |
| 5,395,847 | * 3/1995 | Weinstock et al. | .................. 514/397 |
| 5,444,080 | * 8/1995 | Girard et al. | ........................ 514/397 |

* cited by examiner

*Primary Examiner*—Floyd D. Higel
(74) *Attorney, Agent, or Firm*—Mary E. McCarthy; Stephen Venetianer; Charles M. Kinzig

(57) ABSTRACT

This invention relates to a process for preparing eprosartan by reacting 4-[(2-n-butyl-5-formyl-1H-imidazol-1-yl) methyl]benzoic acid or the bisulfite addition compound of 4-[(2-n-butyl-5-formyl-1H-imidazol-1-yl)methyl]benzoic acid with (2-thienylmethyl)propanedioic acid, mono-ethyl ester.

8 Claims, No Drawings

PROCESS FOR PREPARING EPROSARTAN

This application is a 371 of International Application PCT/US98/02413, filed Feb. 13, 1998, which claims benefit from U.S. Provisional Application 60/038,195, filed Feb. 14, 1997.

FIELD OF THE INVENTION

The present invention relates to a process for preparing eprosartan. This compound is described in U.S. Pat. No. 5,185,351 as being an angiotensin II receptor antagonist useful in the treatment of hypertension, congestive heart failure and renal failure.

BACKGROUND OF THE INVENTION

U.S. Pat. No. 5,185,351 describes processes for the preparation of imidazole compounds. One of the processes described in this application is the reaction of an aldehyde with a substituted half-acid, half-ester derivative of a malonate. Although this process produces the imidazoles claimed therein, there was a need to improve this process when preparing compounds, such as eprosartan, on a commercial scale.

It has now been found that eprosartan can be prepared by reacting 4-[(2-n-butyl-5-formyl-1H-imidazol-1-yl)methyl]benzoic acid or the bisulfite addition compound of 4-[(2-n-butyl-5-formyl-1H-imidazol-1-yl)methyl]benzoic acid (PCT Application WO 95/32189) with (2-thienylmethyl)propanedioic acid, mono-ethyl ester to produce eprosartan efficiently in high yield and high purity. The efficiency of this process and the quality and yield of the imidazole product are particularly important when preparing said product on a large scale for therapeutic use.

DESCRIPTION OF THE INVENTION

The present invention provides a process for the preparation of eprosartan, which is (E)-α-[[2-butyl-1-[(4-carboxyphenyl)methyl]-1H-imidazol-5-yl]methylene]-2-thiophene propanoic acid, a compound of formula (I):

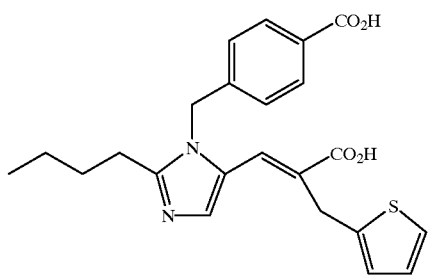

(I)

or a pharmaceutically acceptable salt thereof, which process comprises reacting a compound of formula (II):

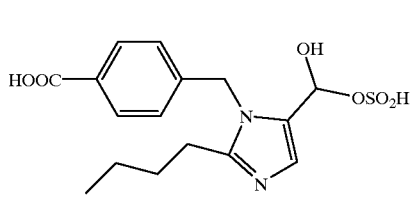

(II)

or an acid or a base addition salt thereof, with a compound of formula (III):

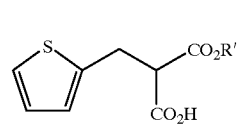

(III)

wherein R' is $C_{1-4}$alkyl, at reduced pressure in the presence of a catalyst, such as piperidine or piperidinium propionate in an excess of propionic acid, and thereafter hydrolyzing the R' ester and optionally forming a pharmaceutically acceptable salt.

Alternately, a formula (I) compound can be prepared by reacting a compound of formula (IV):

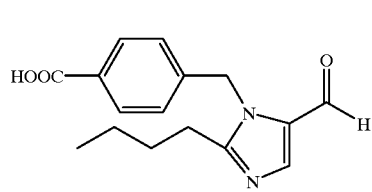

(IV)

with a formula (III) compound at reduced pressure in the presence of a catalyst, such as piperidine or piperidinium propionate in an excess of propionic acid, and thereafter hydrolyzing the R' ester and optionally forming a pharmaceutically acceptable salt.

Acid addition salts of formula (I) and (II) compounds are formed with the appropriate inorganic or organic acids by methods known in the art. Representative examples of suitable acids are maleic, fumaric, acetic, succinic, hydrochloric, hydrobromic, sulfuric, phosphoric or methanesulfonic. Preferably, the pharmaceutically acceptable acid addition salt for the formula (I) compound is the methanesulfonic acid addition salt.

Base addition salts of formula (I) and (II) compounds are formed with the appropriate inorganic or organic bases by methods known in the art. Cationic salts are prepared by treating the parent compound with an excess of an alkaline reagent, such as hydroxide, carbonate or alkoxide, containing the appropriate cation; or with an appropriate organic amine. Representative examples of cations are $Li^+$, $Na^+$, $K^+$, Ca$^{++}$, Mg$^{++}$ and NH$_4^+$. The preferred salt form for the formula (II) compound is

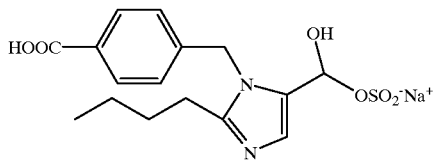

As used herein, C$_{1-4}$alkyl means an alkyl group of 1–4 carbons, branched or unbranched. C$_{1-4}$alkyl includes methyl, ethyl, n-propyl, isopropyl, n-butyl, isobutyl and t-butyl. The preferred R' C$_{1-4}$alkyl group is ethyl.

Typically the process is carried out by combining 4-[(2-n-butyl-5-formyl-1H-imidazol-1-yl)methyl]benzoic acid or the bisulfite addition compound of 4-[(2-n-butyl-5-formyl-1H-imidazol-1-yl)methyl]benzoic acid with (2-thienylmethyl)-propanedioic acid, mono-ethyl ester in a suitable solvent, such as toluene, in the presence of a catalyst, for example, in the presence of piperidinium propionate and an excess of propionic acid, at a suitable temperature, such as at a temperature of about 75° C. to about 100° C., preferably at a temperature of 80° C.–85° C., at reduced pressure, such as at an internal pressure reduced to about 9–13 inches of Hg, preferably 11 inches of Hg. The ester precursors to the formula (I) compound are hydrolyzed to the corresponding formula (I) carboxylic acid using base, such as aqueous sodium or potassium hydroxide. Thereafter, pharmaceutically acceptable salts may be prepared as described above.

Alternately, 4-[(2-n-butyl-5-formyl-1H-imidazol-1-yl)methyl]benzoic acid or the bisulfite addition compound of 4-[(2-n-butyl-5-formyl-1H-imidazol-1-yl)methyl]benzoic acid and (2-thienylmethyl)propanedioic acid, mono-ethyl ester are reacted to give (E)-α-[[2-butyl-1-[(4carboxyphenyl)methyl]-1H-imidazol-5-yl]methylene]-2-thiophene propanoic acid by heating the two substrates in toluene at reflux under reduced pressure and in the presence of piperidine as catalyst followed by hydrolysis of the intermediate ester ethyl (ethyl (E)-α-[[2-butyl-1-[(4-carboxyphenyl)methyl]-1H-imidazol-5-yl]methylene]-2-thiophenepropanoate). In this preparation, 4-[(2-n-butyl-5-formyl-1H-imidazol-1-yl)methyl]benzoic acid or the bisulfite addition compound of 4-[(2-n-butyl-5-formyl-1H-imidazol-1-yl)methyl]benzoic acid, (2-thienylmethyl) propanedioic acid, mono-ethyl ester, and toluene are charged to a glass lined steel vessel and are initially heated to 55–60° C. to afford a homogenous solution. The catalyst (66 mol % piperidine) is added and the reaction is heated to reflux (70–75° C.) under reduced pressure. Reflux conditions are maintained for 20–35 hours and additional (2-thienylmethyl)-propanedioic acid, mono-ethyl ester is added. Once the reaction is complete, water and aqueous sodium hydroxide are added to the vessel and the reaction mixture heated at reflux under atmospheric conditions for 1–3 hours. The reaction is deemed complete when the level of ethyl (E)-α-[[2-butyl-1-[(4-carboxyphenyl)-methyl]-1H-imidazol-5-yl]methylene]-2-thiophene propanoate is less than 2.0%. The reaction is cooled to 45–50° C. and the aqueous and organic phases separated. The toluene phase is discarded. Ethanol is added to the aqueous phase and the solution is acidified with aqueous hydrochloric acid until a pH of 5.0 to 5.4 is achieved, maintaining the temperature at 50–55° C. The product slurry is cooled and allowed to stir at 10–15° C. for 2 hours. The product is isolated by centrifugation, washed and stored. Thereafter, pharmaceutically acceptable salts may be prepared as described above.

The reaction between 4-[(2-n-butyl-5-formyl-1H-imidazol-1-yl)methyl]benzoic acid or the bisulfite addition compound of 4-[(2-n-butyl-5-formyl-1H-imidazol-1-yl) methyl]benzoic acid and (2-thienylmethyl)propanedioic acid, mono-ethyl ester catalyzed with piperidine can be run successfully in solvents (and/or solvent systems) other than toluene; these solvents include cyclohexane, cyclohexane:dichloroethane (12:5 or 1:1), cyclohexane:pyridine (12:5), and cyclohexane:ethyl acetate:pyridine (8:3:1).

Other catalysts which successfully promote the reaction between 4-[(2-n-butyl-5-formyl-1H-imidazol-1-yl)methyl] benzoic acid or the bisulfite addition compound of 4-[(2-n-butyl-5-formyl-1H-imidazol-1-yl)methyl]benzoic acid and (2-thienylmethyl)propanedioic acid, mono-ethyl ester in toluene under reduced pressure besides piperidine include morpholine, 1-methylpiperazine, and pyrrolidine.

The invention is illustrated by the following examples. The examples are not intended to limit the scope of this invention as defined hereinabove and as claimed hereinbelow.

EXAMPLES

Example 1

Preparation of (E)-α-[[2-Butyl-1-[(4-carboxyphenyl)-methyl]-1H-imidazol-5-yl] methylene]-2-thiophene propanoic acid (Eprosartan)

| Reagents and Solvents | | |
|---|---|---|
| 1. Bisulfite addition compound of 4-[(2-n-butyl-5-formyl-1H-imidazol-1-yl)methyl]benzoic acid (68.57% 4-[(2-n-butyl-5-formyl-1H-imidazol-1-yl)methyl]benzoic acid) | 12.03 kg | 28.82 moles |
| 2. (2-Thienylmethyl)propanedioic acid, mono-ethyl ester | 15.29 kg (80.9% w/w assay) | 54.18 moles |
| 3. Piperidine | 2.85 L | 28.82 moles |
| 4. Propionic acid | 8.60 L | 115.28 moles |
| 5. Toluene 56.5 L + 19.0 L = 75.5 L total | | |
| 6. Sodium hydroxide | 16.7 kg (50% aqueous solution) | 208.75 moles |
| 7. Water | 65.0 L | |
| 8. Ethanol | 41.2 kg | |
| 9. 6 N HCl | Adjust to pH 5.0 to 5.2 | |
| 10. Water | 75.0 L | |

Procedure

1. Charge toluene (56.5 L) to the reactor.

2. Charge (2-thienylmethyl)propanedioic acid, monoethyl ester (15.29 kg, 80.9% w/w assay) and bisulfite addition compound of 4-[(2-n-butyl-5-formyl-1H-imidazol-1-yl) methyl]benzoic acid (12.03 kg, 68.57% 4[(2-n-butyl-5-formyl-1H-imidazol-1-yl)methyl]benzoic acid) to the reactor and initiate stirring. Reduce the internal pressure to 11 inches of Hg and heat to reflux (internal temperature of reaction was maintained between 80–85° C.) for 1–2 h. Set the jacket temperature at 110° C. Collect the water in a Dean-Stark trap.

3. Charge toluene (19.0 L) followed by propionic acid (6.45 L, 86.46 mol) to a second reactor. Treat the resulting solution slowly with piperidine (2.85 L, 28.82 mol) at room temperature. Stir the resulting mixture for approximately 30 min.

4. Vent the first reactor with nitrogen and reduce the jacket temperature to 80 C. Transfer the piperidinium propionate-propionic acid solution in toluene from the second reactor to the first reactor. Reduce the internal pressure to 11 inches of Hg and heat to reflux (internal temperature of reaction was maintained between 80–85° C.). Set the jacket temperature at 140° C. Collect the water in a Dean-Stark trap.

5. After 7.5 h, the amount of aldehyde (4-[(2-n-butyl-5-formyl-1H-imidazol-1-yl)methyl]benzoic acid) remaining in solution was about 20% and the amount of (2-thienylmethyl)propanedioic acid, mono-ethyl ester remaining was about 20%. An additional charge of (2-thienylmethyl)propanedioic acid, mono-ethyl ester (1.53 kg, 5.42 mole) was added at the 8.5 h mark.

6. After 13.5 h, the reaction was complete and the reaction was cooled to 70° C. (The amount of aldehyde remaining was about 5%.) Water (65.0 L) and sodium hydroxide (16.7 kg; 50% w/w aqueous solution) was added and the reaction was brought to reflux.

7. The reaction was refluxed for an hour. The reaction was assayed for the presence of ethyl (E)-α-[[2-butyl-1-[(4-carboxyphenyl)methyl]-1H-imidazol-5-yl]methylene]-2-thiophene propanoate. If any is present, reflux for an additional half hour. Repeat assay.

8. Cool the solution to 60 C. Separate the layers and add ethanol (41.2 kg) to the water layer. Slowly adjust the pH of the solution to 5.2 with 6 N HCl (temp. 60° C.). The product will start to crystallize (temp. 60° C.). Cool to room temperature and stir for two hours. Filter and wash the product with water (2×37.5 L).

7. The solid was vacuum dried (9.44 kg, 77.2%).

Analytical Data

| HPLC | |
|---|---|
| Column | Zorbax SB-C18, 3.5 mm, 7.5 cm × 4.6 mm |
| Column Temperature | 40 C. |
| Flow Rate | 2.0 mL/min |
| Sample Preparation | 8 mL of the reaction is blown down with a stream of nitrogen and then dissolved in 2 mL of 50:50 acetonitrile : water |
| Injection Volume | 2.0 mL |
| Detection Wavelength | 235 nm |
| Mobile phase A | 0.1 M Ammonium acetate (pH = 6.7) |
| Mobile phase B | 50:50 0.1 M Ammonium acetate : acetonitile |
| Gradient program | From 0 to 10 minutes, from 100% mobile phase A to 100% mobile phase B in a linear gradient, 5 minutes at 100% mobile phase B, then re-equilibrate for 5 minutes at 100% mobile phase A |
| Run Time | 15 minutes |
| Equilibration Time | 5 minutes |
| Retention time | 4-[(2-n-butyl-5-formyl-1H-imidazol-1-yl)methyl]benzoic acid   4.81 min |
| | (E)-α-[[2-butyl-1-[(4-carboxyphenyl)-methyl]-1H-imidazol-5-yl]methylene]-2-thiophene propanoic acid   4.58 min |
| | (2-thienylmethyl)-propanedioic acid, mono-ethyl ester   4.13 min |
| | ethyl (E)-α-[[2-butyl-1-[(4-carboxyphenyl)-methyl]-1H-imidazol-5-yl]methylene]-2-thiophene propanoate   8.43 min |

Example 2

Preparation of (E)-α-[[2-Butyl-1-[(4-carboxyphenyl)-methyl]-1H-imidazol-5-yl]methylene]-2-thiophene Propanoic Acid (Eprosartan)

A glass-lined steel reaction vessel is charged with 4-[(2-n-butyl-5-formyl-1H-imidazol-1-yl)methyl]benzoic acid, (2-thienylmethyl)propanedioic acid, mono-ethyl ester (about 1.9 molar equivalents relative to assayed 4-[(2-n-butyl-5-formyl-1H-imidazol-1-yl)methyl]benzoic acid), and toluene (about 6.3 g per gram of assayed 4-[(2-n-butyl-5-formyl-1H-imidazol-1-yl)methyl]benzoic acid) and heated to 55–60° C. Piperdine (approximately 66 mol % relative to 4-[(2-n-butyl-5-formyl-1H-imidazol-1-yl)methyl]benzoic acid) is added. The reaction is then heated to reflux with azeotropic removal of water under reduced pressure so that an internal temperature of about 70–75° C. is maintained. The reaction is monitored by IPC 1 for the disappearance of starting 4-[(2-n-butyl-5-formyl-1H-imidazol-1-yl)methyl]benzoic acid. If >10% of the starting 4-[(2-n-butyl-5-formyl-1H-imidazol-1-yl)methyl]benzoic acid remains after 12–30 hours, additional charges of (2-thienylmethyl)propanedioic acid, mono-ethyl ester (0.10 equivalents per charge relative to 4-[(2-n-butyl-5-formyl-1H-imidazol-1-yl)methyl]benzoic acid) may be added and the reaction continued. When IPC 1 analysis indicates that the reaction of starting 4-[(2-n-butyl-5-formyl-1H-imidazol-1-yl)methyl]benzoic acid is essentially complete (<10% remaining), the solution is cooled to about 60–65° C. The cooled solution is treated with demineralized water (6.8 g per gram of assayed 4-[(2-n-butyl-5-formyl-1H-imidazol-1-yl)methyl]benzoic acid) and an aqueous, 6.7 N, solution of sodium hydroxide (about 2.0 ml of solution per gram of assayed 4-[(2-n-butyl-5-formyl-1H-imidazol-1-yl)methyl]benzoic acid) and the mixture is heated at reflux for about 1.0–3.5 hours. The reaction is assayed, by IPC 2, to confirm the complete conversion (<2.0%) to product. The solution is then cooled to about 50° C. and the layers are separated. Ethyl alcohol (about 5.0 g per gram of assayed 4-[(2-n-butyl-5-formyl-1H-imidazol-1-yl)methyl]benzoic acid) is added to the aqueous phase and the pH is adjusted to about 5.0–5.4 with aqueous, 6 N, hydrochloric acid solution. The resulting suspension is stirred at about 10–15° C. for about 2 hours to complete precipitation. The product is isolated by centrifugation, washed twice with water and the wet cake is used directly in the next step. The corrected isolated yield of product at this stage is typically about 70–85%. Assay of a dried sample of product on a w/w basis by HPLC versus a standard sample typically indicates a relative purity of about 97–99%.

Analytical Data

IPC 1

HPLC (Gradient)

Apparatus: The following equipment or its equivalent can be used:

Instrument Hewlett Packard, Model 1050

Pumping System Ternary, low-pressure mixing gradient pump, HP 1050

Injector Autosampler, HP 1050 Series

Detector UV, Variable wavelength, HP 1050 Series

Conditions:

Column Zorbax SB-C18, 7.5 cm×4.6 mm, 3.5 microns particle size, Manufactured by Rockland Technologies, Inc.

US Distributor: MAC-MOD Analytical, Inc.

Dilution Solvent 1:5 Acetonitrile:BPLC Grade Water

Eluent Organic: HPLC grade acetonitrile
Aqueous: 0.1 M Ammonium acetate (pH=6.7)
Mobile Phase Preparation Mobile Phase A=0.1 M Ammonium acetate
Mobile phase B=50:50; 0.1 M Ammonium Acetate:Acetonitrile
Detection Wavelength 235 nm, 0.1 AUFS
Flow Rate 2.0 ml/min.
Temperature 40° C.
Injection Volume 20 microliters
Analysis Time 20 minutes
Re-equilibration Time 6 minutes
Sample Preparation Approximately 30 mg (2 drops) of the reaction mixture is weighed into a 25 ml volumetric flask and dried under a nitrogen stream. The volumetric flask is then filled to volume with dilution solvent. The sample is sonicated for 10 minutes and allowed to cool to room temperature
Gradient Program 1.) Initial Solvent Composition-0% mobile phase B
  2.) Linear Gradient from 0% to 100% mobile phase B in 10 minutes
  3.) Hold at 100% mobile phase B for 5 minutes
  4.) Linear Gradient from 100% to 0% mobile phase B in 5 minutes
  5.) Re-equilibrate at 0% mobile phase B for six minutes.
IPC 2
HPLC (Gradient)
Apparatus: The following equipment or its equivalent can be used:
Instrument Hewlett Packard, Model 1050
Pumping System Ternary, low-pressure mixing gradient pump, HP 1050
Injector Autosampler, HP 1050 Series
Detector V, Variable wavelength, HP 1050 Series
Conditions:
Column Spherisorb SCX, 5 um, 250 mm×4.6 mm
Dilution Solvent 1:5 Acetonitrile:HPLC Grade Water
Eluent Organic: HPLC grade acetonitrile
Aqueous Buffer A: 11.5 g ammonium dihydrogenphosphate dissolved in 1000 mL water adjusted to pH 2.5 with phosphoric acid
Mobile Phase Preparation Mobile Phase A=200 mL Buffer A, 700 mL water, 100 mL acetonitrile
Mobile phase B=200 mL Buffer A, 450 mL water, 350 mL acetonitrile
Detection Wavelength 235 nm
Flow Rate 2.0 ml/min.
Temperature 60° C.
Injection Volume 10 microliters
Analysis Time 20 minutes
Re-equilibration Time 5 minutes
Sample Preparation Transfer 20 mL of the IPC sample into a 50 mL beaker. Stir and, if necessary, add methanol (one to two mL) until the solution is homogenous. Using a Pasteur-pipet, transfer four drops of the IPC-sample (50 uL) into a 25-mL volumetric flask. Dilute with 20 mL of mobile phase B and sonicate for one minute.
Gradient Program 1.) Solvent Composition from 0 to 3 minutes: 0% mobile phase B
  2.) Linear Gradient from 0% to 100% mobile phase B in one minute
  3.) Hold at 100% mobile phase B for 16 minutes
  4.) Linear Gradient from 100% to 0% mobile phase B in 5 minutes
  5.) Re-equilibrate at 0% mobile phase B for 5 minutes.

It is to be understood that the invention is not limited to the embodiments illustrated hereinabove and the right to the illustrated embodiments and all modifications coming within the scope of the following claims is reserved.

What is claimed is:

1. A process for the preparation of eprosartan, a compound of formula (I):

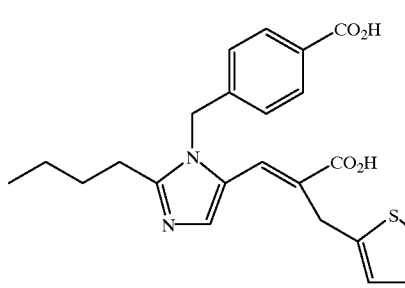

or a pharmaceutically acceptable salt thereof, which process comprises reacting a compound of formula (II):

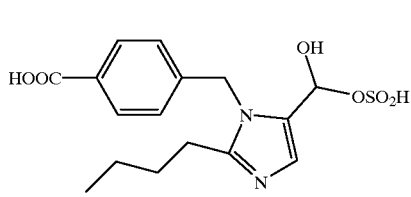

or an acid or a base addition salt thereof, with a compound of formula (III):

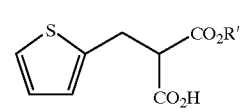

wherein R' is $C_{1-4}$alkyl, at reduced pressure from about 9–13 inches of Hg, in the presence of piperidine or piperidinium propionate and excess propionic acid, and thereafter hydrolyzing the R' ester using base and forming a pharmaceutically acceptable salt.

2. The process according to claim 1 wherein the formula (II) compound is

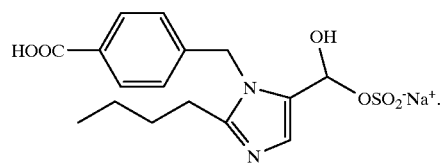

3. The process according to claim 1 wherein the pharmaceutically acceptable salt of the formula (I) compound is the methanesulfonic acid salt.

4. The process according to claim 1 wherein the pressure is reduced to 11 inches of Hg.

5. A process for the preparation of eprosartan, a compound of formula (I):

(I)

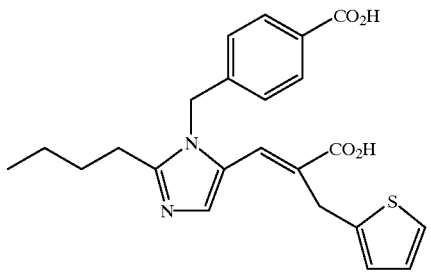

or a pharmaceutically acceptable salt thereof, which process comprises reacting a compound of formula (IV):

(IV)

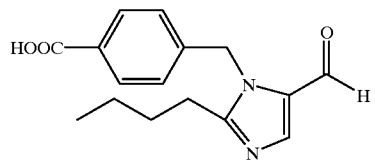

or an acid or a base addition salt thereof, with a compound of formula (III):

(III)

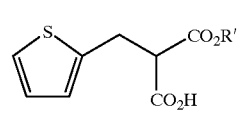

wherein R' is $C_{1-4}$alkyl, at reduced pressure from about 9–13 inches of Hg, in the presence of piperidine or piperidinium propionate and excess propionic acid, and thereafter hydrolyzing the R' ester using base and forming a pharmaceutically acceptable salt.

6. The process according to claim 5 wherein the pharmaceutically acceptable salt of the formula (I) compound is the methanesulfonic acid salt.

7. The process according to claim 5 wherein the pressure is reduced to about 9–13 inches of Hg.

8. The process according to claim 5 wherein the pressure is reduced to 11 inches of Hg.

* * * * *